(12) United States Patent
Zhen et al.

(10) Patent No.: US 9,730,440 B2
(45) Date of Patent: Aug. 15, 2017

(54) COATED POWDER PARTICLES

(71) Applicant: AgroFresh, Inc., Collegeville, PA (US)

(72) Inventors: Yueqian Zhen, Paoli, PA (US); Jeffrey A. Coles, Southampton, NJ (US)

(73) Assignee: Agrofresh Inc., Collegeville, PA (US)

( * ) Notice: Subject to any disclaimer, the term of this patent is extended or adjusted under 35 U.S.C. 154(b) by 0 days.

(21) Appl. No.: 14/296,767

(22) Filed: Jun. 5, 2014

(65) Prior Publication Data

US 2015/0080219 A1 Mar. 19, 2015

Related U.S. Application Data

(63) Continuation-in-part of application No. 13/168,090, filed on Jun. 24, 2011, now abandoned.

(60) Provisional application No. 61/360,968, filed on Jul. 2, 2010.

(51) Int. Cl.
    *A01N 25/26* (2006.01)
    *A01N 27/00* (2006.01)
    *A23B 7/154* (2006.01)

(52) U.S. Cl.
    CPC ............. *A01N 25/26* (2013.01); *A01N 27/00* (2013.01); *A23B 7/154* (2013.01)

(58) Field of Classification Search
    CPC ........ A01N 25/26; A01N 27/00; A01N 25/04; A01N 25/12; A01N 25/28
    USPC ....................................................... 504/357
    See application file for complete search history.

(56) References Cited

U.S. PATENT DOCUMENTS

| | | |
|---|---|---|
| 5,059,434 A | 10/1991 | Kang et al. |
| 5,116,872 A | 5/1992 | Ackermann et al. |
| 5,384,186 A | 1/1995 | Trinh |
| 5,637,350 A | 6/1997 | Ross |
| 5,827,540 A | 10/1998 | Motojima et al. |
| 6,017,849 A | 1/2000 | Daly et al. |
| 2003/0100450 A1 | 5/2003 | Kostansek et al. |
| 2008/0145477 A1 | 6/2008 | Shen et al. |
| 2009/0035380 A1* | 2/2009 | Kostansek .................. 424/498 |

FOREIGN PATENT DOCUMENTS

| | | |
|---|---|---|
| EP | 1 602 276 A1 | 12/2005 |
| WO | 97/07676 | 3/1997 |
| WO | WO 9707676 A1 * | 3/1997 |
| WO | 2004/101668 A2 | 11/2004 |

OTHER PUBLICATIONS

Teunou, "Rotary disc atomisation for microencapsulation applications—prediction of the particle trajectories," Journal of Food Engineering, vol. 71, pp. 345-353, 2005.
U.S. Statutory Invention Registration, Johnson, Reg. No. H1732; (Jun. 2, 1989).

* cited by examiner

*Primary Examiner* — Janet Epps-Smith
*Assistant Examiner* — Courtney Brown
(74) *Attorney, Agent, or Firm* — Barnes & Thornburg LLP

(57) ABSTRACT

There is provided a powder composition comprising a collection of particles (I) having median particle diameter of 10 micrometers to 200 micrometers, wherein each of said particles (I) comprises
    (a) a covering of a fatty compound having melting point of 50° C. to 110° C. and
    (b) one or more inner particles (II) comprising one or more complex that contains a cyclopropene compound molecule or a portion of a cyclopropene compound molecule encapsulated in a molecule of a molecular encapsulating agent.

Also provided is a slurry comprising water and such a powder. Also provided is a method of contacting plants or plant parts with such a slurry.

11 Claims, 1 Drawing Sheet

COATED POWDER PARTICLES

RELATED APPLICATION

This application is a continuation in part of application Ser. No. 13/168,090 filed on Jun. 24, 2011. The nonprovisional application designated above, namely application Ser. No. 13/168,090, filed Jun. 24, 2011, claims the benefit of U.S. Provisional Application No. 61/360,968 filed Jul. 2, 2010, the entire contents of which are incorporated herein by reference.

BACKGROUND

One desirable way of treating plants or plant parts is to prepare a liquid composition that contains one or more cyclopropene compound and then apply that liquid composition to plants or plant parts. It is contemplated that such treatment is useful for blocking the effects of ethylene in the treated plants or plant parts. One useful way of preparing such a liquid composition is to make an encapsulation complex in which a molecule of a cyclopropene compound is encapsulated in a molecule of a molecular encapsulation agent. The encapsulation complex can be made into a powder, which can be conveniently stored and transported. One method of using such a powder is to make a liquid composition by mixing the powder with water, possibly along with other ingredients, and bringing the resulting liquid composition into contact with plants or plant parts, for example by spraying or dipping.

One difficulty that arises with such a method of making and using such liquid compositions is that contact with water may cause the cyclopropene compound to release from the encapsulation complex too quickly. Release of cyclopropene compound that happens too quickly can cause several problems. If the liquid composition is in an enclosed container such as a spray tank, undesirably high levels of cyclopropene compound may accumulate in the headspace of the container. Also, if the liquid composition is sprayed or is placed into an open tank (e.g., an open tank into which plants or plant parts will be dipped), undesirable amounts of cyclopropene compound may be released to the atmosphere and become unavailable for coming into contact with plants or plant parts.

U.S. Pat. No. 5,384,186 describes perfume/cyclodextrin complexes suspended in polyalkylene glycol carrier material.

It is desired to provide a powder composition that contains one or more cyclopropene compound and that, when mixed with water, retards the release of cyclopropene compound but does not entirely prevent the release of cyclopropene compound.

SUMMARY OF INVENTION

In a first aspect of the present invention, there is provided a powder composition comprising a collection of particles (I) having median particle diameter between 10 micrometers and 200 micrometers, wherein each of said particles (I) comprises
(a) a covering of a fatty compound having melting point(s) between 50° C. and 110° C. and
(b) one or more inner particles (II) comprising one or more complex that contains a cyclopropene compound molecule or a portion of a cyclopropene compound molecule encapsulated in a molecule of a molecular encapsulating agent.

In one embodiment, the powder composition comprises inner particles (II) comprising one or more complex that contains a cyclopropene compound molecule or a portion of a cyclopropene compound molecule encapsulated in a molecule of a molecular encapsulating agent. In another embodiment, the fatty compound is selected from the group consisting of hydrogenated soybean oil, hydrogenated cottonseed oil, carnauba wax, microcrystalline wax, or combinations thereof. In another embodiment, the collection of particles (I) has median particle diameter between 10 micrometers and 100 micrometers. In another embodiment, the fatty compound has melting point between 70° C. and 90° C. In another embodiment, final melting temperature of the fatty compound does not exceed 90° C. In another embodiment, the amount of said fatty compound is from 50% to 99% by weight based on the weight of the powder composition. In another embodiment, the powder composition further comprises one or more dispersant.

In one embodiment, the hydrogenated soybean oil comprises Dritex S. In another embodiment, the hydrogenated cottonseed oil comprises Dritex C. In another embodiment, the microcrystalline wax or a carnauba wax/microcrystalline wax mixture comprises microcrystalline wax 963. In another embodiment, the powder composition additionally comprises one or more polymer. In a further embodiment, the one or more polymer comprises Polywax™ 500.

In another aspect of the present invention, provided is a slurry comprising an aqueous medium and a collection of particles (I) having median particle diameter between 10 micrometers and 200 micrometers. The particles (I) comprises (i) a covering of a fatty compound having melting point between 50° C. and 110° C. and; (ii) one or more inner particles (II) comprising one or more complex that contains a cyclopropene compound molecule or a portion of a cyclopropene compound molecule encapsulated in a molecule of a molecular encapsulating agent.

In one embodiment, the powder composition comprises inner particles (II) comprising one or more complex that contains a cyclopropene compound molecule or a portion of a cyclopropene compound molecule encapsulated in a molecule of a molecular encapsulating agent. In another embodiment, the fatty compound is selected from the group consisting of hydrogenated soybean oil, hydrogenated cottonseed oil, carnauba wax, microcrystalline wax, or combinations thereof. In another embodiment, the collection of particles (I) has median particle diameter between 10 micrometers and 100 micrometers. In another embodiment, the fatty compound has melting point between 70° C. and 90° C. In another embodiment, final melting temperature of the fatty compound does not exceed 90° C. In another embodiment, the amount of said fatty compound is from 50% to 99% by weight based on the weight of the powder composition. In another embodiment, the powder composition further comprises one or more dispersant.

In one embodiment, the hydrogenated soybean oil comprises Dritex S. In another embodiment, the hydrogenated cottonseed oil comprises Dritex C. In another embodiment, the microcrystalline wax or a carnauba wax/microcrystalline wax mixture comprises microcrystalline wax 963. In another embodiment, the powder composition additionally comprises one or more polymer. In a further embodiment, the one or more polymer comprises Polywax™ 500.

In another aspect of the present invention, provided is a method of treating plants or plant parts comprising contacting the plants or plant parts with a slurry comprising an aqueous medium and a collection of particles (I) having median particle diameter between 10 micrometers and 200 micrometers. The particles (I) comprises (i) a covering of a fatty compound having melting point between 50° C. and 110° C. and; (ii) one or more inner particles (II) comprising one or more complex that contains a cyclopropene compound molecule or a portion of a cyclopropene compound molecule encapsulated in a molecule of a molecular encapsulating agent.

In one embodiment, the powder composition comprises inner particles (II) comprising one or more complex that contains a cyclopropene compound molecule or a portion of a cyclopropene compound molecule encapsulated in a molecule of a molecular encapsulating agent. In another embodiment, the fatty compound is selected from the group consisting of hydrogenated soybean oil, hydrogenated cottonseed oil, carnauba wax, microcrystalline wax, or combinations thereof. In another embodiment, the collection of particles (I) has median particle diameter between 10 micrometers and 100 micrometers. In another embodiment, the fatty compound has melting point between 70° C. and 90° C. In another embodiment, final melting temperature of the fatty compound does not exceed 90° C. In another embodiment, the amount of said fatty compound is from 50% to 99% by weight based on the weight of the powder composition. In another embodiment, the powder composition further comprises one or more dispersant.

In one embodiment, the hydrogenated soybean oil comprises Dritex S. In another embodiment, the hydrogenated cottonseed oil comprises Dritex C. In another embodiment, the microcrystalline wax or a carnauba wax/microcrystalline wax mixture comprises microcrystalline wax 963. In another embodiment, the powder composition additionally comprises one or more polymer. In a further embodiment, the one or more polymer comprises Polywax™ 500.

DETAILED DESCRIPTION OF THE INVENTION

Figure 1:
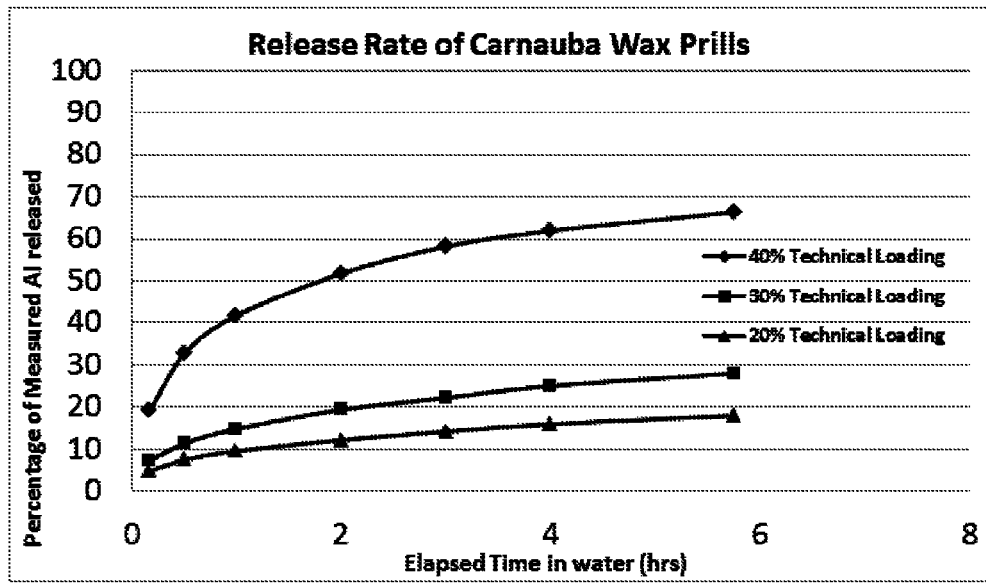
FIG. 1 shows representative 1-methylcyclopropene (1-MCP) release profiles using coated particles (prills) made of carnauba wax.

As used herein, a "fatty group" is a chemical group that contains at least one chain of carbon atoms that is at least 8 carbon atoms long. A "fatty compound" is any compound that contains a fatty group.

As used herein, and "aqueous medium" is a composition that is liquid at 25° C. and that contains 75% or more water by weight, based on the weight of the aqueous medium. Ingredients that are dissolved in the aqueous medium are considered to be part of the aqueous medium, but materials that are not dissolved in the aqueous medium are not considered to be part of the aqueous medium. An ingredient is "dissolved" in a liquid if individual molecules of that ingredient are distributed throughout the liquid and are in intimate contact with the molecules of the liquid.

As used herein, when any ratio is said to be X:1 or higher, that ratio is meant to be Y:1, where Y is X or higher. Similarly, when any ratio is said to be R:1 or lower, that ratio is meant to be S:1, where S is R or lower.

As used herein, the "aspect ratio" of a solid particle is the ratio of the particle's longest dimension to that particle's shortest dimension. A particle's longest dimension is the length of the longest possible line segment ("segment L") that passes through the particle's center of mass and that has each of its end points on the surface of the particle. That particle's shortest dimension is the length of the shortest possible line segment ("segment S") that passes through the particle's center of mass, that has each of its end points on the surface of the particle, and that is perpendicular to segment L. The aspect ratio is the ratio of the length of segment L to the length of segment S.

As used herein, the "diameter" of a particle is the average of the length of that particle's segment L and that particle's segment S. It is noted that, when the particle is spherical, this definition give the "diameter" in the usual sense.

As used herein, when a property of a powder is described as having a "median" value, it is contemplated that half of the total volume of powder particles will consist of particles that have that property with value above that median value and that half of the total volume of powder particles will consist of particles that have property with value below that median value.

The practice of the present invention involves the use of one or more cyclopropene compound. As used herein, a cyclopropene compound is any compound with the formula

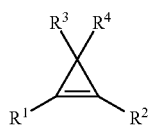

where each $R^1$, $R^2$, $R^3$ and $R^4$ is independently selected from the group consisting of H and a chemical group of the formula:

$$-(L)_n\text{-}Z$$

where n is an integer from 0 to 12. Each L is a bivalent radical. Suitable L groups include, for example, radicals containing one or more atoms selected from H, B, C, N, O, P, S, Si, or mixtures thereof. The atoms within an L group may be connected to each other by single bonds, double bonds, triple bonds, or mixtures thereof. Each L group may be linear, branched, cyclic, or a combination thereof. In any one R group (i.e., any one of $R^1$, $R^2$, $R^3$ and $R^4$) the total number of heteroatoms (i.e., atoms that are neither H nor C) is from 0 to 6. Independently, in any one R group the total number of non-hydrogen atoms is 50 or less. Each Z is a monovalent radical. Each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G, is a 3 to 14 membered ring system.

$R^1$, $R^2$, $R^3$, and $R^4$ groups are independently selected from the suitable groups. Among the groups that are suitable for use as one or more of $R^1$, $R^2$, $R^3$, and $R^4$ are, for example, aliphatic groups, aliphatic-oxy groups, alkylphosphonato groups, cycloaliphatic groups, cycloalkylsulfonyl groups, cycloalkylamino groups, heterocyclic groups, aryl groups, heteroaryl groups, halogens, silyl groups, other groups, and mixtures and combinations thereof. Groups that are suitable for use as one or more of $R^1$, $R^2$, $R^3$, and $R^4$ may be substituted or unsubstituted.

Among the suitable $R^1$, $R^2$, $R^3$, and $R^4$ groups are, for example, aliphatic groups. Some suitable aliphatic groups include, for example, alkyl, alkenyl, and alkynyl groups. Suitable aliphatic groups may be linear, branched, cyclic, or a combination thereof. Independently, suitable aliphatic groups may be substituted or unsubstituted.

As used herein, a chemical group of interest is said to be "substituted" if one or more hydrogen atoms of the chemical group of interest is replaced by a substituent.

Also among the suitable $R^1$, $R^2$, $R^3$, and $R^4$ groups are, for example, substituted and unsubstituted heterocyclyl groups that are connected to the cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, for example, substituted and unsubstituted heterocyclic groups that are connected to the cyclopropene compound through an intervening oxy group, amino group, carbonyl group, sulfonyl group, thioalkyl group, or aminosulfonyl group; examples of such $R^1$, $R^2$, $R^3$, and groups are diheteroarylamino, heteroarylthioalkyl, and diheteroarylaminosulfonyl.

Also among the suitable $R^1$, $R^2$, $R^3$, and $R^4$ groups are, for example, hydrogen, fluoro, chloro, bromo, iodo, cyano, nitro, nitroso, azido, chlorato, bromato, iodato, isocyanate, isocyanido, isothiocyanato, pentafluorothio; acetoxy, carboethoxy, cyanato, nitrato, nitrito, perchlorato, alkenyl, butylmercapto, diethylphosphonato, dimethyphenylsilyl, isoquinolyl, mercapto, naphthyl, phenoxy, phenyl, piperidino, pyridyl, quinolyl, triethylsilyl, trimethylsilyl; and substituted analogs thereof.

As used herein, the chemical group G is a 3 to 14 membered ring system. Ring systems suitable as chemical group G may be substituted or unsubstituted; they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring systems suitable as chemical group G may be monocyclic, bicyclic, tricyclic, polycyclic, spiro, or fused; among suitable chemical group G ring systems that are bicyclic, tricyclic, or fused, the various rings in a single chemical group G may be all the same type or may be of two or more types (for example, an aromatic ring may be fused with an aliphatic ring).

In preferred embodiments, one or more of $R^1$, $R^2$, $R^3$, and $R^4$ is hydrogen or $(C_1-C_{10})$ alkyl. More preferred are embodiments in which each of $R^1$, $R^2$, $R^3$, and $R^4$ is hydrogen or $(C_1-C_8)$ alkyl. More preferred are embodiments in which each of $R^1$, $R^2$, $R^3$, and $R^4$ is hydrogen or $(C_1-C_4)$ alkyl. More preferred are embodiments in which each of $R^1$, $R^2$, $R^3$, and $R^4$ is hydrogen or methyl. More preferred are embodiments in which $R^1$ is $(C_1-C_4)$ alkyl and each of $R^2$, $R^3$, and $R^4$ is hydrogen. Most preferred are embodiments in which $R^1$ is methyl and each of $R^2$, $R^3$, and $R^4$ is hydrogen, and the cyclopropene compound is known herein as "1-MCP."

Preferred are embodiments in which a cyclopropene compound is used that has boiling point at one atmosphere pressure of 50° C. or lower; more preferred 25° C. or lower; more preferred 15° C. or lower. Independently, embodiments are preferred in which a cyclopropene compound is used that has boiling point at one atmosphere pressure of −100° C. or higher; more preferred −50° C. or higher; more preferred −25° C. or higher; more preferred 0° C. or higher.

The composition of the present invention includes at least one molecular encapsulating agent. In preferred embodiments, at least one molecular encapsulating agent encapsulates one or more cyclopropene compound or a portion of one or more cyclopropene compound. A complex that contains a cyclopropene compound molecule or a portion of a cyclopropene compound molecule encapsulated in a molecule of a molecular encapsulating agent is known herein as a "cyclopropene compound complex."

In preferred embodiments, at least one cyclopropene compound complex is present that is an inclusion complex. In such an inclusion complex, the molecular encapsulating agent forms a cavity, and the cyclopropene compound or a portion of the cyclopropene compound is located within that cavity.

Preferably, in such inclusion complexes, the interior of the cavity of the molecular encapsulating agent is substantially apolar or hydrophobic or both, and the cyclopropene compound (or the portion of the cyclopropene compound located within that cavity) is also substantially apolar or hydrophobic or both. While the present invention is not limited to any particular theory or mechanism, it is contemplated that, in such apolar cyclopropene compound complexes, van der Waals forces, or hydrophobic interactions, or both, cause the cyclopropene compound molecule or portion thereof to remain within the cavity of the molecular encapsulating agent.

The amount of molecular encapsulating agent can usefully be characterized by the ratio of moles of molecular encapsulating agent to moles of cyclopropene compound. In preferred embodiments, the ratio of moles of molecular encapsulating agent to moles of cyclopropene compound is 0.1 or larger; more preferably 0.2 or larger; more preferably 0.5 or larger; more preferably 0.9 or larger. Independently, in preferred embodiments, the ratio of moles of molecular encapsulating agent to moles cyclopropene compound is 10 or lower; more preferably 5 or lower; more preferably 2 or lower; more preferably 1.5 or lower.

Suitable molecular encapsulating agents include, for example, organic and inorganic molecular encapsulating agents. Preferred are organic molecular encapsulating agents, which include, for example, substituted cyclodextrins, unsubstituted cyclodextrins, and crown ethers. Suitable inorganic molecular encapsulating agents include, for example, zeolites. Mixtures of suitable molecular encapsulating agents are also suitable. In preferred embodiments, the encapsulating agent is alpha-cyclodextrin, beta-cyclodextrin, gamma-cyclodextrin, or a mixture thereof. In more preferred embodiments of the invention, alpha-cyclodextrin is used.

A preferred method of making the powder composition of the present invention includes the step of making a powder (herein called the "complex powder") that contains cyclopropene compound complex. The complex powder either contains no fatty compound or else, if any fatty compound is present, the amount of all fatty compounds is less than 1% by weight based on the weight of the complex powder. Usually, each particle of the complex powder contains many molecules of molecular encapsulating agent in which a molecule of a cyclopropene compound is encapsulated. The complex powder may also contain one or more adjuvants, including, for example, one or more mono- or di-saccharide compound, one or more metal complexing agent, or combinations thereof.

Preferred complex powders have median particle diameter of 10 micrometers or less; more preferred 7 micrometers or less; more preferred 5 micrometers or less. Independently, preferred complex powders have median particle diameter of 0.1 micrometer or more; or 0.3 micrometer or more. Median particle diameter may be measured by light diffraction using a commercial instrument such as those manufactured, for example, by Horiba Co. or Malvern Instruments.

Preferred complex powders have median aspect ratio of 5:1 or lower; more preferably 3:1 or lower; more preferably 2:1 or lower. If a complex powder is obtained that has undesirably high median aspect ratio, it is preferred to use mechanical means such as, for example, milling, to reduce the median aspect ratio to a desirable value.

The present invention involves the use of a fatty compound having melting point of 50° C. to 110° C. If a fatty compound has more than one melting point, the "melting point" of that fatty compound is herein considered to be the lowest melting point that accounts for 10% or more of the total melting exotherm. Melting points and melting exotherms may be observed using differential scanning calorimetry (DSC).

Fatty compounds include, for example, fatty acids, fatty hydrocarbons, fatty oils and waxes, modified versions thereof, and mixtures thereof. Suitable modifications include any process, including chemical reactions, that alters the composition of a fatty compound, as long as the resulting compound still meets the definition of fatty compound. Modifications include, for example, hydrogenation, esterification, trans-esterification, de-esterification, polymerization, attachment of functional groups, and combinations thereof. Fatty acids have the formula R—COOH, where the R group contains a fatty group. Fatty hydrocarbons are fatty compounds that contain only carbon and hydrogen atoms. Fatty oils and waxes are fatty compounds that contain one or more ester group, hydroxyl group, aldehyde group, ketone group, or combination thereof.

Preferred fatty compounds include at least one fatty group having 16 or more carbon atoms. More preferred are fatty compounds that include at least one fatty group having 18 or more carbon atoms.

Preferred fatty compounds include fatty acids, triglycerides, polyolefin waxes, and mixtures thereof. Triglycerides are triesters of glycerol with three fatty acids. Among fatty acids, the preferred fatty acids do not have pendant hydroxyl groups. When oils that contain carbon-carbon double bonds are hydrogenated, the extent of the hydrogenation process can determine the melting point of the hydrogenated oil. It is contemplated that when hydrogenated oil is used in the present invention, the extent of hydrogenation will be determined to make the melting point of the hydrogenated oil fall within the melting point ranges discussed below as appropriate for use in the present invention. Preferred triglycerides are hydrogenated soybean oil and hydrogenated cottonseed oil.

Polyolefin waxes are polymers that have polymerized units of ethylene, propylene, or a mixture thereof. Preferred polyolefin waxes are polymers that have no polymerized units other than ethylene, propylene, or a mixture thereof. More preferred are polyethylene homopolymer waxes. Independent of monomer type, preferred polyolefin waxes have number-average molecular weight of 200 or higher; more preferred is 400 or higher. Independently, preferred polyolefin waxes have number-average molecular weight of 2,000 or lower; or 1,000 or lower; or 750 or lower.

Preferred fatty compounds are triglycerides, polyolefin waxes, and mixtures thereof.

Fatty compounds useful in the present invention have melting point of 50° C. to 110° C. It is contemplated that if the melting point is too low, the powder composition will be sticky, and the powder will not flow properly. It is also contemplated that if the melting point is too high, when cyclopropene compound complex is mixed with molten fatty compound, the temperature will be high enough to cause significant degradation of the cyclopropene compound.

Preferred fatty compounds have melting point of 55° C. or higher; more preferred 65° C. or higher; more preferred 70° C. or higher. Independently, preferred fatty compounds have melting point of 100° C. or lower; more preferred 90° C. or lower.

Another method of assessing fatty compounds is the temperature of onset of the melting point. To determine the onset temperature, the exotherm curve (heat flow vs. temperature) produced by the DSC for the melting point transition is observed. The baseline is determined, and a corrected heat-flow curve calculated by subtracting the baseline from the original heat-flow curve. The maximum heat-flow value of the corrected curve (HFMAX) is determined. The onset temperature is the lowest temperature at which the heat-flow value on the corrected curve is equal to 0.1*HFMAX.

Preferred fatty compounds have onset temperature of 45° C. or higher; more preferred is 55° C. or higher.

In the powder composition of the present invention, within an individual powder particle, a fatty compound forms a covering over inner particles (II) that contain cyclopropene compound complex.

A preferred method of making the powder composition of the present invention involves mixing complex powder with molten fatty compound. This mixture may then be separated into individual powder particles by any method. A preferred method of turning the molten mixture into powder particles is spray chilling. Spray chilling is a process that involves forming droplets of the molten mixture and dispersing those droplets in air; as the droplets fall due to gravity, they cool and form solid powder particles. The air may be still or may be given an upward current. The droplets may be formed by passing the molten mixture through a spray head or a nozzle or by flinging molten mixture off of a rotating disk by centrifugal force.

An alternative method of producing powder particles of the present invention is non-aqueous spray drying. In this method, using a solvent other than water, fatty compound is dissolved and complex powder is dispersed, and the resulting mixture is spray dried.

When powder particles of the present invention are formed by any of the above methods, it is contemplated that complex powder particles remain intact and become the inner particles (II) within each of the powder particles of the present invention.

In the powder particles (I) of the present invention, it is contemplated that the outer surface of each powder particle (I) is composed mostly or entirely of the fatty compound. It is contemplated that, for most or all of the powder particles (I), each powder particle (I) contains one or more particles of complex powder (i.e., powder particles (II)).

Preferred powder compositions of the present invention contain one or more dispersant. Dispersants are compounds that assist in suspending solid particles in a liquid medium. Typical dispersants are polymeric or oligomeric. It is contemplated that a dispersant will aid in distributing the powder particles (II) throughout the liquid form of the fatty compound (i.e., molten or dissolved fatty compound) during the process of forming the powder particles (I). The preferred amount of dispersant is, by weight based on the weight of the powder composition of the present invention, 0.05% or more; more preferably 0.1% or more; more preferably 0.2% or more. Independently, the preferred amount of is, by weight based on the weight of the powder composition of the present invention, 5% or less; or 2% or less.

Some powder compositions of the present invention contain one or more "additional polymer" in addition to the fatty compound having melting point of 50° C. to 110° C. Such an additional polymer may or may not qualify as a fatty compound having melting point of 50° C. to 110° C. Preferred additional polymers are miscible with the fatty compound having melting point of 50° C. to 110° C., while that fatty compound is in the melt state.

In one preferred embodiment, the fatty compound having melting point of 50° C. to 110° C. contains one or more hydrogenated triglyceride and an additional polymer. In such embodiments, preferred polymers are copolymers of olefin monomer with one or more non-olefin monomer. Preferred non-olefin monomers are vinyl esters of aliphatic carboxylic acids and unsaturated carboxylic acids. Preferred additional polymers have relatively high molecular weight. Molecular weight can be judged by melt flow rate, using ASTM D1238, at 190° C. with 2.16 kg. Preferred additional polymers have melt flow rate of 1 g/10 min or higher; more (preferably 3 g/10 or higher. Independently, preferred additional polymers have melt flow rate of 20 g/10 min or lower; or 10 g/10 min or lower.

The amount of fatty compound in the powder composition of the present invention, by weight based on the weight of the powder composition, is preferably 40% or more; more preferably 50% or more. Independently, the amount of fatty compound in the powder composition of the present invention, by weight based on the weight of the powder composition, is preferably 99% or less; more preferably 95% or less.

One useful way to characterize the powder composition of the present invention is the median particle diameter, which is 10 to 200 micrometers. The median particle diameter is preferably 150 micrometers or less; more preferably 100 micrometers or less; more preferably 75 micrometers or less; more preferably 60 micrometers or less.

Another useful way to characterize the powder composition of the present invention is to measure dQ, where Q is a number less than 100. In a particular collection of powder particles, powder particles representing Q % of the total volume of all the powder particles will have particle diameter of less than dQ, while powder particles representing (100-Q) % of the total volume of all the powder particles will have particle diameter of more than dQ.

The powder composition of the present invention preferably has d90 of 100 micrometers or less; more preferably 50 micrometers or less. Independently, the powder composition of the present invention preferably has d10 of 1 micrometer or more; more preferably 3 micrometers or more.

The powder composition of the present invention may be altered to form an intermediate solid composition or an intermediate liquid composition or a combination thereof. An intermediate solid composition is a solid composition made from the powder composition of the present invention, optionally by a method that includes mixing the powder composition of the present invention with additional ingredients; some intermediate solid compositions are particulate compositions with larger or smaller particle size than the powder composition of the present invention. For another example, the powder composition of the present invention may be mixed with a liquid, either an aqueous medium or some other liquid, to form an intermediate liquid composition; such an intermediate liquid composition may or may not be further diluted prior to contact with plants or plant parts.

The powder composition of the present invention may be used for treating plants or plant parts in any way. For example, the powder composition may be mixed with other materials or may be used directly.

The preferred method of using the powder composition of the present invention is to use it to form an aqueous slurry. An aqueous slurry is formed when the powder composition is mixed with an aqueous medium. To form such a slurry, the aqueous medium may be mixed directly with the powder composition of the present invention or with one of the intermediate compositions described herein above. It is expected that the particles (I) of the powder composition remain intact in the slurry. It is also contemplated that most or all of the particles (I) will be dispersed in the slurry as individual particles rather than as agglomerates thereof. The particles (I) may require mechanical agitation to remain suspended in the aqueous medium, or they may remain suspended without agitation.

The amount of powder composition in the slurry may be characterized by the concentration of cyclopropene compound in the slurry. Preferred slurries have cyclopropene compound concentration, in units of milligrams of cyclopropene compound per liter of slurry, of 2 or higher; more preferably 5 or higher; more preferably 10 or higher. Independently, preferred slurries have cyclopropene compound concentration, in units of milligrams of cyclopropene compound per liter of slurry, of 1000 or lower; more preferably 500 or lower; more preferably 200 or lower.

The amount of water in the aqueous medium used in the slurry is, by weight based on the weight of aqueous medium, 80% or more; or 90% or more; or 95% or more.

The slurry may optionally contain one or more adjuvants, such as, for example, one or more metal complexing agent, one or more surfactant, one or more oil, one or more alcohol, or mixtures thereof. Preferred metal-complexing agents, if used, are chelating agents. Preferred surfactants, if used, are anionic surfactants and silicone surfactants. Preferred alcohols, if used, are alkyl alcohols with 4 or fewer carbon atoms. Oils are compounds that are liquid at 25° C. are not water, are not surfactants, and are not alcohols. Preferred oils, if used, are hydrocarbon oils and silicone oils.

The preferred method of treating plants is to bring the slurry into contact with plants or plant parts. Such contacting may be performed in any location, including inside enclosed spaces (such as, for example, containers, rooms, or buildings) or outside of any enclosed space. Preferably, such contacting is performed outside of any enclosed space. As used herein, "outside of any enclosed space" means outside of any building or enclosure or else in a room or building that is ventilated to outdoor atmosphere. More preferred is performing such contacting outside of any building or enclosure. More preferred is performing such contacting in an outdoor field or plot.

The slurry of the present invention may be brought into contact with plants or plant parts by any method. Preferred methods include dipping plant parts into the slurry and applying slurry to plants or plant parts by spraying, foaming, brushing, or combinations thereof. More preferred are spraying the slurry onto plants or plant parts and dipping plant parts into the slurry. More preferred is spraying the slurry onto plants or plant parts.

Plants or plant parts may be treated in the practice of the present invention. Preferred is treatment of whole plants;

more preferred is treatment of whole plants while they are planted in soil, prior to the harvesting of useful plant parts.

Any plants that provide useful plant parts may be treated in the practice of the present invention. Preferred are plants that provide fruits, vegetables, and grains.

In addition to the use of hydrogenated soybean oil (for example Dritex S) and/or hydrogenated cotton oil (for example Dritex C), carnauba wax alone or mixture of carnauba wax with the above hydrogenated vegetable oils and/or with microcrystalline wax are also preferred as the waxy material to protect the active ingredient, 1-Methyl Cyclopropene, (1-MCP) in the 1-MCP-cyclodextrin complex (known as HAIP) against moisture.

The advantages of using natural carnauba wax or its synthetic equivalent include (1) carnauba wax has a higher and narrower melting range than Dritex S and Dritex C or Microcrystalline wax, etc., which allows the prills (coated particles) and the final products to withstand higher storage temperatures (for example 54° C.). The encapsulated particles made with carnauba wax alone or as a mixture are more thermally stable at elevated storage temperature (for example 54° C.) than other waxy material, including Dritex S and/or Dritex C, alone. Therefore, carnauba wax and its synthetic equivalent are most preferred as the waxy material for encapsulation; and (2) encapsulations made with carnauba wax are, at least equally, effective in protecting the active ingredient 1-MCP as other wax materials do, including hydrogenated vegetable oils.

Regarding the melting point for the fatty compounds useful for the subject invention, natural carnauba wax has a higher initial melting point than most other waxes tested, which enables the encapsulation formulation made of carnauba wax to withstand a higher storage temperature without causing the product to melt or sticky. Melting of the wax causes individual encapsulation particle to stick together, rendering the formulation unsprayable.

As an example, Differential scanning calorimetry (DSC) for a preparation of carnauba wax shows the preparation starts to melt soften at about 55° C., significant melting starting at ~70° C., and has a sharp melting point at around 82° C., and melt completely when the temperature is close to 90° C. Carnauba wax appears the one of the least sticky waxes under 54° C. storage conditions among all waxes tested.

Certain waxes, either melt at a much lower initial melting temperature or at a much higher final melting temperature or both. The higher final melting temperature has at least two disadvantages (1) it requires unnecessarily higher energy and operating cost, and (2) it also would potentially degrade the active more severely during processing. Thus, in one embodiment, waxes with a final melting temperature above 90° C. are excluded.

The DSC for a preparation of commercial wax—Microcrystalline wax 963, (from Frank B Ross Co., Inc, 97041 New Brunswick Avenue Rahway, N.J.), shows that the preparation starts to melt at around 40° C. and completely melts at 100° C., with a wider and less desirable 40° C.-100° C. melting range than carnauba wax. Its low initial melting temperature (~40° C.) suggests these micronized wax particles or encapsulation made of this wax, would become sticky at temperature near ~40° C. This product would require a lower temperature for storage in order to minimize clumps formation.

The DSC for a synthetic polymer, Polywax 500, (from Baker Hughes, 12645 W. Airport Blvd. Sugar Land, Tex. 77478-5050) starts to melt around 30-35° C. Thus, particles made of this polywax 500 material alone would start to become sticky at above 40° C. and requires a lower storage temperature.

The DSC of a preparation of hydrogenated cotton oil, Dritex C, shows that the preparation starts to melt around 50° C. and completely melted when the temperature is close to 80° C. It is less sticky than Polywax 500 at 45-50° C. storage conditions (hence more thermally stable than Polywax 500).

The DSC of a preparation of waxy material Trancendium 180, (from Caravan Ingredients, 7905 Quivira Road, Lenexa, Kans. 66215), shows that the preparation has a very sharp/narrower melting range. It completely melts when the temperature is close to 70° C. However, it starts to melt and soften at around 30° C. Thus, micronized particles made of this waxy material alone may form clumps under 54° C. storage conditions.

It is to be understood that for purposes of the following Examples that each operation disclosed herein is performed at 25° C. unless otherwise specified.

EXAMPLES

In the following Examples, the following abbreviations are used:

FC50=any fatty compound having melting point of 50° C. to 110° C.

AP1=powder containing 1-MCP encapsulated in alpha-cyclodextrin, with concentration of 1-MCP of 4.5% by weight, and approximately 5% water, by weight. Milled until d50 was 2 to 5 micrometers.

WX1=Dritex™ S, hydrogenated soybean oil, from ACH Food & Nutrition Co.

WX2=Polywax™ 500 polyethylene wax, from Baker Hughes Inc.

DP1=Atlox™ 4914 dispersant, a nonionic polymer, from Croda Co.

DP2=Agrimer™ AL-22, dispersant, alkylated vinylpyrrolidone copolymers, from International Specialty Products Corp.

PY1=Elvax™ 4355 terpolymer of ethylene/vinyl acetate/acid from DuPont Co.

SS1=Silwet™ L-77 surfactant, based on a trisiloxane ethoxylate, from Momentive Performance Materials, Inc.

SS2=Aerosil™ OT-B surfactant powder, from Cytek Industries, Inc.

SLS sodium lauryl Sulfate

SOL1 solution in distilled water of 0.05% by weight based on the weight of SOL1, of each of SS1 and SLS.

Procedure P1—Production of Coated Powder: Powder AP1 was mixed into the molten FC50 under the minimum needed temperature at the desired weight ratio. Other additives, such as dispersants and plasticizer may be added at this time, if desired. The mixture was agitated with a Cowles disc disperser to achieve dispersion of the solids in the mixture. This mixture was then atomized with pressured air. The particles solidified quickly and were collected in a cyclone. The particle size was controlled by a combination of air pressure, molten wax temperature and composition, and the additives.

Procedure P2—Evaluation of the release of 1-MCP: A composition containing water and wetting agents and 1-MCP was placed into a 250 ml bottle. The bottle quickly was sealed either with a PTFE/silicone crimp seal via a crimper or with a Mininert™ valve (Supelco Company) on a screw. Both setups allow the sampling of the inside headspace by a syringe and also allow the re-seal of the valve after repeated sampling.

The bottles were placed on top of a shaker and the shaker swirled at a rate of approximately 120 revolutions per minute. The headspace inside the bottle was sampled at pre-determined time intervals and analyzed on an analytical gas chromatograph with the proper column. The amount of 1-MCP that was released into the headspace was calculated based on its concentration and the volume of the headspace. The percentage of 1-MCP released was calculated from the total 1-MCP present in the sample.

Example 1

Comparative Formulation CF11 was a comparative formulation, made using powder AP1 and other ingredients but no FC50. The concentration of 1-MCP in Comparative Formulation CF11 was 1% by weight, based on the weight of CF11. 0.06 gram of CF11 and 10 ml of SOL1 (to give a solution in which the concentration of 1-MCP was 50 mg per liter of solution.) were added to a 250 ml bottle. The release of 1-MCP was measured using procedure P2.

Formulation F12 was made as follows. Coated Powder was made using AP1 (10% by weight) and stearic acid (90% by weight) in Procedure P1. 0.2 gram of the coated powder was added to a 250 ml bottle containing 10 ml of SOL1. The amount of AP1 was chosen to yield a solution having approximately 50 mg of 1-MCP per liter of solution. The release of 1-MCP was measured using procedure P2. Results are shown in Table 1, where Formulation F12 had slower release of 1-MCP than Comparative Formulation CF11.

TABLE 1

1-MCP release profiles of CF11 and F12.

| CF11 | | F12 | |
|---|---|---|---|
| time (min) | % 1-MPC released | time (min) | % 1-MCP released |
| 3.5 | 41 | 3 | 17 |
| 6.5 | 51 | 6 | 26 |
| 10 | 60 | 10 | 33 |
| 15 | 70 | 15 | 40 |
| 20 | 76 | 25 | 46 |
| 25 | 78 | 40 | 53 |
| 30 | 86 | 60 | 57 |
| 40 | 93 | 90 | 63 |
| 50 | 96 | 120 | 69 |
| 60 | 100 | 166 | 73 |
| 75 | 100 | 210 | 75 |
| | | 240 | 82 |

Example 2

Effect of Particle Size

Formulation F21 was made as follows. Coated Powder was made using AP1 (10% by weight) and WX1 (90% by weight) in Procedure P1, using conditions adjusted to yield coated powder with median particle diameter of 30 micrometers. The coated powder (0.14 gram) was added to a 250 ml bottle containing 10 ml of SOL1. The amount of AP1 was chosen to yield a formulation having approximately 50 mg of 1-MCP per liter of formulation.

Formulation F22 was made identically to F21, except that the conditions in Procedure P1 were chosen to yield coated powder with median particle diameter of 60 micrometers. The formulations were tested by Procedure P2. Results are shown in Table 2, where Formulation F22 had slower release of 1-MCP than Formulation F21.

TABLE 2

1-MCP release profiles of F21 and F22.

| F21 (30 micrometers) | | F22 (60 micrometers) | |
|---|---|---|---|
| time (min) | % 1-MPC released | time (min) | % 1-MCP released |
| 10 | 20 | 10 | 9 |
| 30 | 32 | 30 | 16 |
| 60 | 44 | 60 | 22 |
| 120 | 53 | 120 | 30 |
| 195 | 59 | 195 | 38 |
| 1200 | 77 | 1200 | 67 |

Example 3

Headspace in a Commercial Spray Tank

Tests were conducted using the tank of a Hardi™ ES-50 commercial sprayer. The capacity of the tank was 191 liter (50 gallon).

Comparative Formulation CF31 was identical to CF11. CF31 was added to 191 liters of tap water in the tank. Concentration of 1-MCP in the tank was 25 mg/liter.

Formulation F32 was made as follows. Coated Powder was made using AP1 (10% by weight), WX1 (89.5% by weight), and DP1 (0.5% DP1), using Procedure P1. The powder blend was made as follows: Coated powder was blended with 1.9% (by weight based on the weight of powder blend) SLS (powder) and 4.8% SS2 (by weight based on the weight of powder blend). 191 liter of tap water containing 0.025% SS1, by volume based on the volume of the tap water, was added to the tank. Then some of the water was removed and used to form a slurry with Formulation F32, and the slurry was then added to the remaining water in the tank, with agitation. Concentration of 1-MCP in the tank was 25 mg/liter.

In each case, after the formulation (either CF31 or F32) was added to the tank, the tank was sealed, and 1 ml gas samples were drawn from the headspace port in the tank lid with gas-tight syringes, and the gas samples were analyzed using gas chromatography, reported in "ppm," which is parts by volume of 1-MCP per million parts by volume of air. Results are shown in Table 3, where Formulation F32 releases 1-MCP much more slowly than the comparative formulation CF31.

TABLE 3

1-MCP release profiles of CF31 and F32 (Headspace ppm of 1-MCP).

| time(hr) | CF31 | F32 |
|---|---|---|
| 0.5 | 1983 | 867 |
| 1 | 3254 | 1343 |
| 2 | 6692 | 2297 |
| 4 | 13331 | 3714 |
| 6 | | 4937 |
| 9 | | 6767 |

Example 4

Wax Variations

Coated Powders were made using Procedure P1. 0.6 gram of each coated powder was added to 10 ml of SOL1 and placed in a 250 ml bottle and analyzed using procedure P2. The coated powders (by weight percent) are listed in Table 4.

TABLE 4

Sample preparations

| Coated Powder | AP1 | WX1 | WX2 | DP2 | PY1 |
|---|---|---|---|---|---|
| F41 | 20 | 79.5 | 0 | 0.5 | 0 |
| F42 | 20 | 77.5 | 0 | 0.5 | 2 |
| F43 | 20 | 0 | 79.5 | 0.5 | 0 |

Results of 1-MCP release for these samples are shown in Table 5, where all three show acceptably slow release of 1-MCP.

TABLE 5

1-MCP release profiles of F41, F42, and F43.

| F41 | | F42 | | F43 | |
|---|---|---|---|---|---|
| time (min) | % 1-MCP released | time (min) | % 1-MCP released | time (min) | % 1-MCP released |
| 10 | 6.8 | 10 | 4.7 | 11 | 7.8 |
| 30 | 13.4 | 31 | 9.1 | 31 | 10.4 |
| 60 | 16.7 | 60 | 11.9 | 61 | 12.4 |
| 120 | 20.0 | 120 | 14.8 | 121 | 16.2 |
| 180 | 22.7 | 251 | 18.7 | 192 | 18.8 |
| 300 | 26.1 | 360 | 21.4 | 301 | 21.7 |
| 390 | 28.2 | 1380 | 31.9 | 391 | 24.0 |
| 1380 | 37.2 | | | 1381 | 33.8 |

Example 5

Further Wax Comparisons

Coated Powders were made using Procedure P1. 0.1 gram of each coated powder was added to 10 ml of SOL1 and placed in a 250 ml bottle and analyzed using procedure P2. The coated powders (by weight percent) are listed in Table 6.

TABLE 6

Sample preparations

| Coated Powder | AP1 | WX1 | WX2 | DP2 |
|---|---|---|---|---|
| F51 | 10 | 89.5 | 0 | 0.5 |
| F52 | 10 | 0 | 89.5 | 0.5 |
| F53 | 30 | 69.25 | 0 | 0.75 |
| F54 | 30 | 0 | 69.25 | 0.75 |

Results of 1-MCP release for these samples are shown in Table 7, where all four show acceptably slow release of 1-MCP.

TABLE 7

1-MCP release profiles of F51, F52, F53, and F54.

| F51 | | F52 | | F53 | | F54 | |
|---|---|---|---|---|---|---|---|
| time (min) | % 1-MCP released | time (min) | % 1-MCP released | time (min) | % 1-MCP released | time (min) | % 1-MCP released |
| 10 | 7 | 10 | 6 | 10 | 12 | 10 | 12 |
| 30 | 13 | 30 | 9 | 30 | 19 | 30 | 16 |
| 60 | 16 | 60.5 | 12 | 60 | 23 | 60.5 | 19 |
| 120 | 21 | 122 | 16 | 120 | 28 | 121 | 23 |
| 180 | 23 | 180 | 20 | 180 | 33 | 181 | 26 |
| 360 | 31 | 360 | 26 | 300 | 38 | 301 | 29 |
| 1380 | 44 | 1380 | 35 | 420 | 43 | 421 | 32 |
| | | | | 1441 | 60 | 1441 | 42 |

Example 6

Tomato Epinasty Testing

Tomato epinasty tests were performed as follows: Tomatoes (Rutgers 39 Variety Harris Seeds No 885 Lot 37729-A3) were grown in 2½" square pots filled with a commercial potting mix. Two seeds were place in each pot. Plants that had expanded first true leaves and were between 3 and 5 inches high were used for the tomato epinasty test. To conduct the assay, a group of pots was placed on a table in a spray booth, and a moving nozzle sprayed a liquid spray composition onto the plants, which were then allowed to dry in a greenhouse.

After a waiting period of 3 days, treated and untreated plants were placed into a plastic box and sealed. To the box, ethylene was injected through a septum, which gave a concentration of 14 ppm. The plants were held sealed for 12-14 hours in the dark with ethylene in the atmosphere. At the end of ethylene treatment, the box was opened and scored for epinasty. The petiole angle of the third leaf is reported. For each type of treatment, five replicate plants were tested, and the average is reported.

Comparative Formulation CF61 contained 1-MCP encapsulated in alpha-cyclodextrin and contained oil but no FC50. DF61 was mixed with water prior to spraying. Coated Powders were made by Procedure P1 as follows: Coated Powder F62 was the same as F32, including blending with SLS and SS1, as described herein above in Example 3. Coated Powder F63 was prepared the same way as F62, including blending with SLS and SS1, except that, the coated powder in F63 contained 69.25% WX1, 30% AP1, and 0.75% DP2, by weight based on the weight of the coated powder. Each of F62 and F63 was placed in a solution; that solution was 0.038% SS1 in water, by volume based on the volume of the solution. CF61 was placed in water. The spray treatments were all conducted under the same mechanical spray conditions. For each treatment, the concentration of formulation or powder in the solution was adjusted to give the spray rate (in grams of 1-MCP per hectare) that is shown below. Results (average petiole angle) of the control plants were as follows:

Untreated (no exposure to ethylene and no spray treatment): 60 degrees

Unsprayed (exposure to ethylene but no spray treatment): 127 degrees

TABLE 8

Test results on plants

| Sample | SR = 10[1] Angle[2] | SR = 20[1] Angle[2] | SR = 40[1] Angle[2] |
|---|---|---|---|
| CF61 | 127 | 115 | 113 |
| F62 | 99 | 92 | 83 |
| F63 | 114 | 106 | 70 |

Note
[1]Spray Rate, in grams of 1-MCP per hectare

Note
[2]degrees

Results of the test plants are shown in Table 8. The examples of the present invention show reduced petiole angle, demonstrating that the treatment with those example formulations hocks the effect of ethylene, allowing the treated plants to behave more like the plants that were not exposed to ethylene.

Example 7

Different preparations of protecting the active ingredient from immediate release by various encapsulation compositions, after addition to an aqueous solution, are carried out (1) 1-MCP Release rate of 20%, 30% and 40% HAIP protected by carnauba wax alone; and (2) 1-MCP Release rate of 30% and 35% HAIP protected by carnauba wax and by a mixture of 75% Carnauba wax and 25% microcrystalline wax.

Prills (coated particles of for example encapsulated 1-MCP) made of carnauba wax and mixtures of carnauba wax with other waxy material, can protect the active significantly and slow down the release rate of the active ingredient, 1-MCP, delivering the desired profile for the active ingredient, for example 1-MCP.

Encapsulated particles made of carnauba wax and alpha-cyclodextrin (alpha-CD)-1-MCP complex (HAIP), including a blend of 2.5% (wt) Aerosil R-972 and 97.5% (wt) prill that contains about 40% HAIP and ca. 60% carnauba wax, can withstand a storage temperature of 54° C. for two (2) weeks without forming clumps. However, similar mixtures of 2.5% Aerosil R-972 and 97.5% prills made of other waxes, for example Trancendim 180 under the same conditions, formed significant amounts of dumps upon storage at 54° C. elevated temperature. The formation of clumps at elevated temperature could make a formulation completely unsprayable and make a formulation less useful, when stored at such elevated temperatures. A lower storage temperature is required for products containing such waxes, for example Trancendim 180. However, a lower storage temperature requirement makes these waxy materials less attractive than carnauba wax in the market place.

Representative 1-MCP release profiles using prills made of Carnauba wax and 20-40% HAIP provide significant protection of HAIP upon mixing into an aqueous solution (for example reduced rate of release) as shown in FIG. 1. Similar results are shown in Table 9 (time versus % active released into water under various loading conditions).

TABLE 9

Representative 1-MCP release rates of prills (coated particles) made of carnauba wax.

| Time in water (hours) | 20% technical loading | 30% technical loading | 40% Technical Loading |
|---|---|---|---|
| 0.17 | 5 | 7 | 19 |
| 0.5 | 7 | 11 | 33 |
| 1 | 10 | 15 | 42 |
| 2 | 12 | 19 | 52 |
| 3 | 14 | 22 | 58 |
| 4 | 16 | 25 | 62 |
| 6 | 18 | 28 | 66 |

Figure 2:
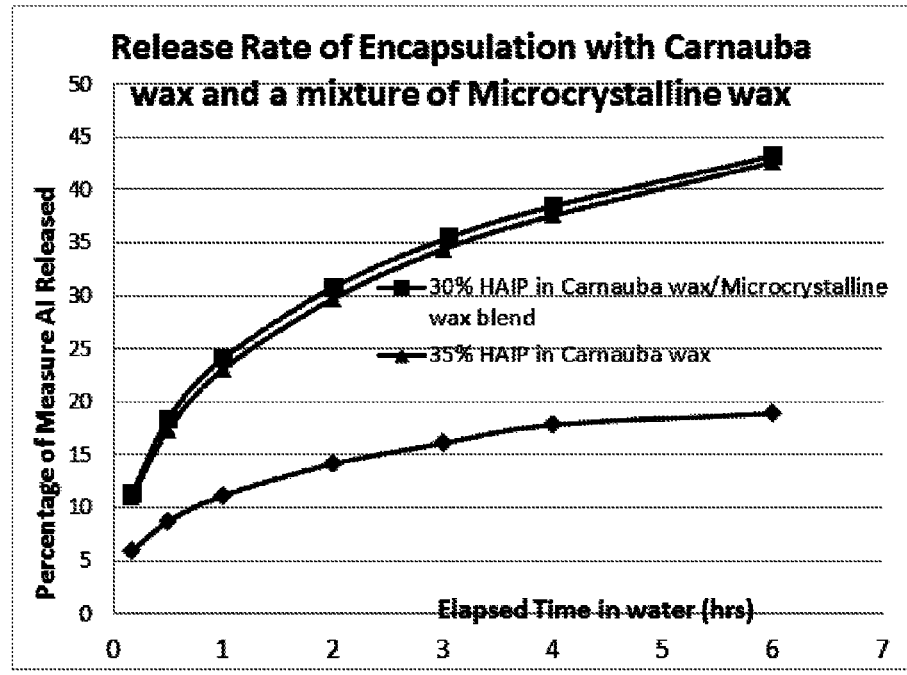
FIG. 2 shows comparative 1-methylcyclopropene (1-MCP) release profiles using coated particles (prills) made of (1) carnauba wax and (2) a mixture of carnauba wax and microcrystalline wax.

Comparative 1-MCP release profiles using prills made of (1) carnauba wax only a 30% and 35% HAIP loading, and (2) a 3:1 (wt) ratio mixture of carnauba wax and microcrystalline wax 5088A (from IGI International) with 30% HAIP loading, are shown in FIG. 2. Similar results are shown in Table 10 (time (hours) versus % active released into water).

TABLE 10

Representative 1-MCP release rates of prills (coated particles) made of carnauba wax and a mixture of carnauba wax and microcrystalline wax.

| Time in water (hours) | 30% Technical loading-in Carnauba wax | 35% Technical loading in carnauba wax | 30% technical loading in mixture of carnauba wax and Microcrystalline wax |
|---|---|---|---|
| 0.17 | 6 | 11 | 11 |
| 0.5 | 9 | 17 | 18 |
| 1 | 11 | 23 | 24 |
| 2 | 14 | 30 | 31 |
| 3 | 16 | 34 | 36 |
| 4 | 18 | 38 | 38 |
| 6 | 19 | 43 | 43 |

Either carnauba wax alone or a mixture of carnauba wax and microcrystalline wax (for example at 3:1 ratio) can provide good protection for the active ingredient (for example 1-MCP) immediate release by water. Carnauba wax alone appears a higher level of protection than its 3:1 mixture with microcrystalline wax (at 30% HAIP loading, the prills made of carnauba wax release 1-MCP more slowly than the wax mixture at the same 30% HAIP loading).

We claim:

1. A powder composition comprising a collection of particles (I) having a median particle diameter of 10 micrometers to 200 micrometers, wherein each of said particles (I) comprises:
    (a) a covering of a fatty compound having a melting point of 50° C. to 110° C., wherein the fatty compound is selected from the group consisting of hydrogenated soybean oil, hydrogenated cottonseed oil, carnauba wax, microcrystalline wax, or combinations thereof, and
    (b) a plurality of inner particles (II) comprising one or more complex that contains a cyclopropene compound molecule or a portion of a cyclopropene compound molecule encapsulated in a molecule of a molecular encapsulating agent.

2. The powder composition of claim 1, wherein the collection of particles (I) has a median particle diameter of 10 micrometers to 100 micrometers.

3. The powder composition of claim 1, wherein the fatty compound has a melting point of 55° C. to 90° C.

4. The powder composition of claim 1, wherein the hydrogenated soybean oil comprises Dritex S.

5. The powder composition of claim 1, wherein the hydrogenated cottonseed oil comprises Dritex C.

6. The powder composition of claim 1, wherein the microcrystalline wax or carnauba wax mixture comprises microcrystalline wax 963.

7. The powder composition of claim 1, wherein the amount of the fatty compound is 50% to 99% by weight based on the weight of the powder composition.

8. The powder composition of claim 1, wherein the powder composition further comprises one or more dispersant.

9. The powder composition of claim 1, wherein the powder composition additionally comprises one or more polymer.

10. The powder composition of claim 9, wherein the one or more polymer comprises a polyethylene wax.

11. A slurry comprising an aqueous medium and a collection of particles (I) having a median particle diameter of 10 micrometers to 200 micrometers, wherein each of said particles (I) comprises:

(a) a covering of a fatty compound having a melting point of 50° C. to 110° C., wherein the fatty compound is selected from the group consisting of hydrogenated soybean oil, hydrogenated cottonseed oil, carnauba wax, microcrystalline wax, or combinations thereof; and (b) a plurality of inner particles (II) comprising one or more complex that contains a cyclopropene compound molecule or a portion of a cyclopropene compound molecule encapsulated in a molecule of a molecular encapsulating agent.

* * * * *